United States Patent [19]

Gleich et al.

[11] Patent Number: 4,710,475

[45] Date of Patent: Dec. 1, 1987

[54] METHOD FOR THE DETERMINATION OF THE IMMINENCE OF LABOR

[75] Inventors: Gerald J. Gleich; Terri L. Wasmoen, both of Rochester, Minn.

[73] Assignee: Mayo Medical Resources, Rochester, Minn.

[21] Appl. No.: 862,451

[22] Filed: May 12, 1986

[51] Int. Cl.⁴ .................... G01N 33/48; G01N 33/49; G01N 33/493
[52] U.S. Cl. ........................................ 436/86; 436/65; 436/906
[58] Field of Search ........................... 436/86, 906, 65

[56] References Cited

PUBLICATIONS

D. E. Maddox et al., J. Exp. Med., 158, 1211–1226 (1983).
D. E. Maddox et al., J. Exp. Med., 160, 29–41 (1984).
D. L. Wassom et al., J. Clin. Invest., 67, 651–661 (1981).

*Primary Examiner*—Kenneth M. Schor
*Assistant Examiner*—Lori-Ann Cody
*Attorney, Agent, or Firm*—Merchant, Gould, Smith, Edell, Welter & Schmidt

[57] ABSTRACT

A method is disclosed for determining whether or not preterm or end-term labor is imminent which is based upon the relative elevation of the level of eosinophil major basic protein (MBP). The level of MBP in a sample of a physiological fluid of a pregnant woman is measured and the level is compared to a predetermined level indicative of the plateau gestational level of the protein.

4 Claims, 3 Drawing Figures

METHOD FOR THE DETERMINATION OF THE IMMINENCE OF LABOR

BACKGROUND OF THE INVENTION

The mechanism regulating the onset of human parturition has been the subjet of intense investigation over the past decade, but remains one of the most elusive regulatory problems in reproductive physiology. Most studies have dealt with the control of uterine contractility but recently, emphasis has also been placed on the regulation of cervical softening and dilatation.

Existing animal models are not adequate to elucidate the human labor process. In animal species such as the sheep, the fetus plays a fundamental role in the physiological onset of labor. The signal for the spontaneous onset of labor is a rise in fetal plasma cortisol levels and this is followed by a fall in maternal progesterone and an increase in maternal estrogen concentrations. The change in the ratio of estrogens to progesterone seems to promote the release of prostaglandins from the placenta and other intrauterine tissues, and the prostaglandins stimulate uterine contractility and the onset of labor. In sheep, the integrity of the fetal pituitary and adrenal is essential for the spontaneous onset of labor, and the ovine placenta, under the influence of fetal cortisol, has the ability to convert progesterone to estrogen. This sequence of endocrine events is not detectable in human pregnancy.

Parturition in women occurs without apparent changes in either free or protein bound 17$\beta$-estradiol and progesterone in plasms or in myometrial tissue. Maternal plasma levels of estradiol and progesterone have been measured in an attempt to predict which patients would deliver preterm, but this approach has failed.

Therefore, it seems likely that human parturition results from some signal or combination of signals, acting on inter-related endocrine and biochemical mechanisms, operating mainly with the uterus. These mechanisms probably operated within the decidua and fetal membranes, are established well before term, but are not normally activated until full term. Since the mechanism is still unknown, however, it has not heretofore been possible to reliably predict either the imminence of labor at term or the imminence of preterm labor.

Preterm labor occurs in little more than 5% of pregnancies but causes 85% of early neonatal deaths not associated with lethal fetal abnormality. One approach to the prediction of preterm labor has been to measure the contractions of the uterus in combination with the regular assessment of cervical dilatation and effacement. However, the validity of these procedures is in dispute. Vaginal examination in pregnancy has been shown to raise prostaglandin levels in the maternal circulation within minutes of this procedure. Since prostaglandins are known to be implicated in uterine contractility, repeated vaginal examinations might provoke preterm labor rather than helping to prevent it.

Furthermore, false positives in the prediction of preterm labor can cause undue anxiety for a large number of women and can lead obstetricians to intervene unnecessarily with "invasive" preventive measures such as tocolytic drugs or cervical cerclage. Since such interventions may themselves have dangers for either mother or fetus, the need for developing improved methods of discriminating women at risk of preterm birth is obvious.

Methods for the prediction of the imminence of term labor would also serve to relieve anxiety and would lead to improved medical care planning, particularly in the case of women who elect to travel in the third trimester.

BRIEF DESCRIPTION OF THE INVENTION

The present invention is directed to a method for determining whether or not labor is imminent which is based upon the measurement of the relative levels of eosinophil major basic protein (MBP) in the physiological fluids of a pregnant woman. More specifically, the present invention provides a method for determining the imminence of labor in a pregnant woman comprising:

(a) determining the level of MBP in a sample of a physiological fluid of said pregnant woman; and (b) comparing said value to a predetermined value indicative of the plateau gestational MBP level in said fluid after about 20 weeks of pregnancy, to determine if a rise in the normal MBP level has occurred which is indicative of the imminence of labor.

The present method is based upon our discovery that the MBP levels present in the physiological fluids such as serum, plasma, saliva, urine and the like of a pregnant woman, become stabilized at an elevated level after about week 20 of gestation. This stabilized level which is attained after about 20 weeks of gestation will be hereinafter referred to as the "plateau gestational level" of MBP in the pertinent physiological fluid. The MBP level undergoes an additional rapid rise over the plateau MBP level at the onset of the biological events which lead to labor. The MBP levels peak near the time of parturition, and then fall to normal. Therefore, the present invention is particularly useful to detect a point of time within the gestational period which is within 1-2 weeks of the onset of term labor. The present invention is also useful to detect the imminence of preterm labor, e.g., labor occurring before 37 weeks. See WHO, *Acta Obstet. Gynecol. Scand.*, 59, 247 (1977).

The plateau gestational level of MBP in a population of pregnant women can vary widely, e.g., between about 1500–8000 ng/ml of serum or plasma. Furthermore, the absolute level of MBP can vary from the average gestational value determined for a given woman. For example, a rise in the MBP level to about 10% above the average gestational level generally is not indicative of the onset of labor. Therefore, the percent rise in the MBP level which is diagnostic for the imminence of labor is dependent on both the accuracy of the determination of the average plateau gestation MBP level and its stability. Preferably, the plateau gestational MBP level is derived from a determination of the MBP levels in a series of fluid samples. The samples are preferably obtained and assayed during about 20–33 weeks of gestation, e.g., at weekly or bimonthly intervals. In accordance with this methodology, a rise of at least about 25–30% in the average MBP level can be considered diagnostic for the onset of labor.

Our analysis of the mean weekly MBP levels derived from the analysis of 413 serum samples taken from 397 pregnant women had previously confirmed that (i) MBP levels were elevated early in gestation, (ii) peaked rapidly to about a 10-fold elevation above normal by the end of the first trimester, and remained relatively close to that level for the remainder of gestation. See D. E. Maddox et al., *J. Exp. Med.*, 158, 1211 (1983). However, the mean weekly MBP values which were obtained at weeks 20–41 did not exhibit a near-time rise which was considered to be diagnostic of the imminence of labor. For example, the mean MBP levels at weeks 37 and 41 were not statistically different. (See Maddox et al. supra, at FIG. 3).

The discovery that a secondary rise in the average gestational MBP levels occurs which is indicative of the imminence of labor resulted from a detailed analysis of the kinetic changes in MBP levels that occur in individual women during pregnancy. Plasma MBP levels were measured by radioimmunoassay in seventeen women from week 32 of gestation to six weeks postpartum. Fourteen of the women experienced a spontaneous onset of labor that was preceded by dramatic increases in plasma MPB levels above the plateau gestational level. Three of the women were oxytocin-induced to end gestation and in all of these women, a late rise in MBP did not occur. MBP levels returned to normal by six weeks postpartum in all women studied, with a half life of 12.5 days. These data confirm for the first time that a rise in average gestational plasma MBP levels late in pregnancy is diagnostic for the imminent onset of labor.

DETAILED DESCRIPTION OF THE INVENTION

Figure 1:
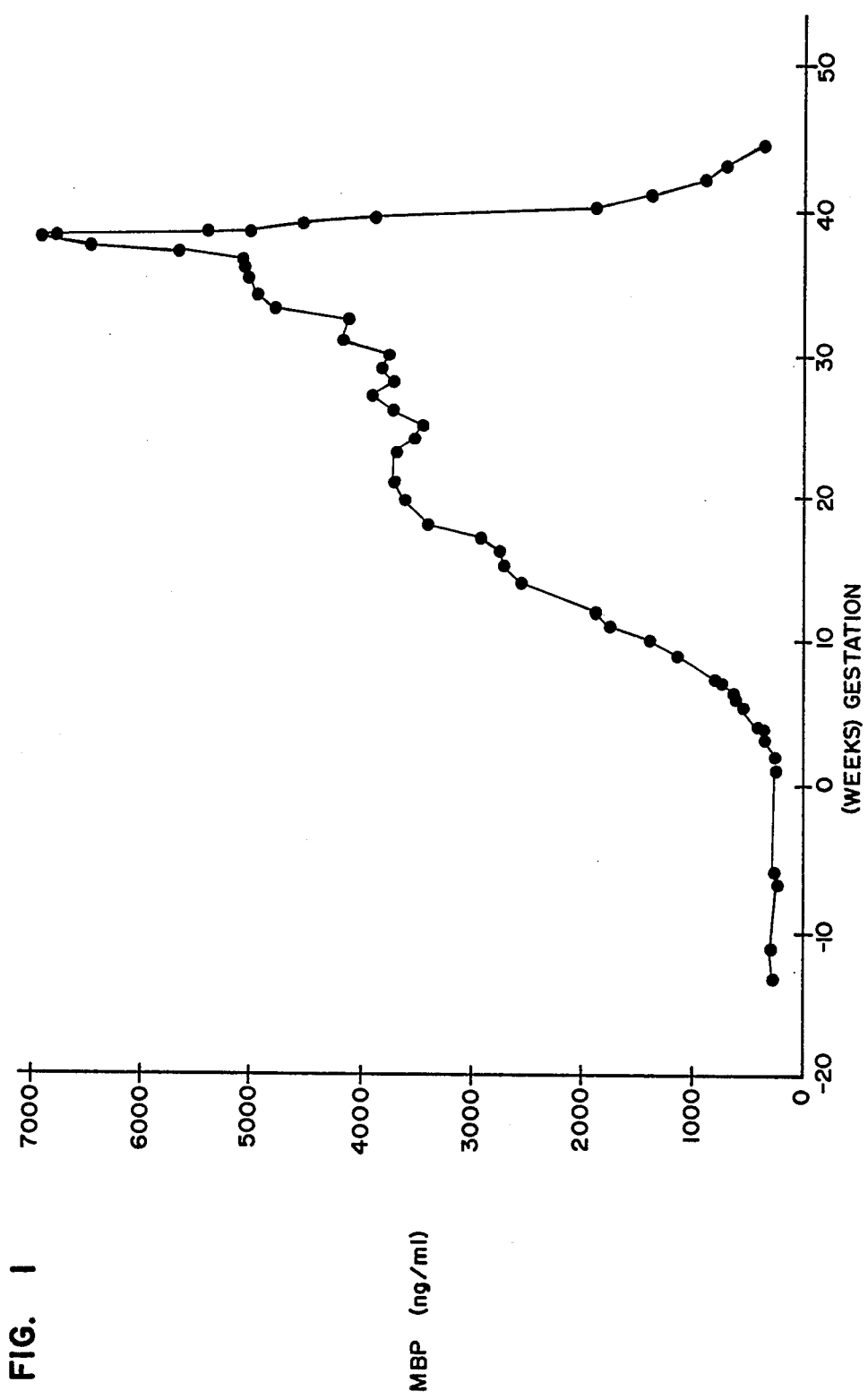
FIG. 1 is a graphical depiction of the plasma MBP levels determined during the course of pregnancy in one woman.

The invention will be further described by reference to the following detailed example.

EXAMPLE

DETERMINATION OF SERUM MBP KINETICS

A. Materials and Methods

1. Plasmas.

Women with a "normal" pregnancy through midterm were recruited for this study using informed consent. Patient histories were reviewed in order to determine gestational age, sex and weight of fetus plus maternal age, parity, and description of labor and delivery. Gestational age was calculated from last menstrual period and ultrasound determined biparietal diameter (Bpd). Two ml of venous blood was drawn into EDTA anticoagulant, centrifuged and the plasmas were stored at $-20°$ C. In women blood samples were drawn at weekly intervals from 32 weeks of gestation through six weeks postpartum, including one sample drawn upon admission to the labor suite. In one women, blood samples were drawn at weekly intervals throughout pregnancy, and every third day during the last two weeks before labor.

2. Plasma Reduction and Alkylation.

The interaction of MBP with plasma carrier proteins via disulfide linkages makes it desirable to reduce and alkylate plasma to increase the sensitivity of the immunological detection of this protein. Therefore, a 0.05 ml portion of plasma was diluted in 0.13 ml of 0.1M tris[hydroxymethylamino]methane, 0.12M NaCl and 0.01M EDTA (TRIS-EDTA buffer, pH 8.1). Dithiothreitol (DTT, 0.02 ml 0.075M) (Sigma Chemical Co., St. Louis) in TRIS-EDTA buffer was added to a final concentration of 7.5 mM DTT and the mixture was incubated for 1 hour at $22°$ C. A 0.02 ml portion of 0.15M iodoacetamide in TRIS-EDTA buffer was added (final concentration = 14 mM iodoacetamide) and incubation was continued for 20 minutes at $22°$ C. Samples were analyzed immediately for MBP by radioimmunoassay (RIA).

3. Radioimmunoassay for MBP. A competitive binding radioimmunoassay using a mouse monoclonal antibody to MBP (J14 7A2) was employed. A sample of the hybridoma which secretes antibody J14 7A2 has been deposited with the American Type Culture Collection, Rockville, Md., USA and has been assigned accession number HB 9089. The monoclonal antibody was prepurified with staphylococcus protein A (Sigma Chemical Co.) by the procedure of D. E. Maddox, et al., *J. Exp. Med.*, 158, 1211 (1983). FAST sticks (Falcon Labware, Becton-Dickenson) were coated with the protein-A purified monoclonal antibody (10 microgram/ml in PBS) for 2 hours at $22°$ C. on a rocking platform. Unbound sites were blocked with PPF-E coating buffer (0.1M $Na_2HPO_4$-$KH_2PO_4$, pH 7.4; 0.15M NaCl, 0.1% protamine sulfate, 1% fetal calf serum, 0.1M EDTA and 0.1% $NaN_3$) for 1 hour at $22°$ C. on a rocking platform. Samples of unknown plasma and samples containing a known amount of eosinophil granule MBP (prepared as described by D. L. Wassom et al., in *J. Clin. Invest.*, 67, 651 (1981)) were reduced and alkylated and diluted in PPF-E. MBP was radiolabeled using the chloramine T method (McConahey et al., *Int. Arch. Allerg. Appln. Immunol.*, 29, 185 (1966)) to a specific activity of 35 mCi/microgram. For dose response curves, serial two-fold dilutions of plasmas or MBP were used. Quantitation employed a standard curve of 0.3–7.0 ng MBP/ml. One hundred microliters of the unknown or of the standard sample (run in duplicate) were placed in wells of a 96-well flat bottom plate and incubated with the antibody-coated sticks for 30 minutes at $22°$ C. One hundred microliters of $^{125}$I-MBP (5 ng/ml in PPF-E) were added to each sample well and incubated with the immobilized antibody sticks overnight at $4°$ C. on a rocking platform. The sticks were washed with phosphate-buffered saline (PBS) containing 0.05% Polysorbate 20, snapped off, and counted in a gamma counter. RIA data was analyzed using a computer program (Hewlett Packard 9845-14254). Nonspecific binding was measured by incubating PPF-E coated sticks with $^{125}$I-MBP. Internal standards consisted of plasma from a normal male and a patient with hypereosinophilic syndrome. Dose response curves were analyed using a regression analysis program (Hewlett Packard 9845-15031). All plasma samples from a given woman were analyzed at one time to minimize any interassay variation.

Similar MBP quantitation was observed using the polyclonal antibody RIA described by Maddox et al., *J. Exp. Med.*, 158, 1211 (1983) and by Wassom et al., *J. Clin Invest.*, 67, 651 (1981), the disclosures of which are incorporated by reference herein.

B. Results

FIG. 1 summarizes the plasma MBP concentration changes determined during pregnancy for one woman. In this subject, MBP levels were clearly above baseline by 4 weeks postconception and showed a steady increase through approximately 20 weeks gestation. From 20 to 33 weeks, the MBP level remained substantially constant. This was followed by a "late rise" in MBP with the largest increase occurring during the last week before parturition. The late-term increase in MBP accounted for 54% of the total increase. The MBP levels then fell rapidly after parturition, which occurred in week 38.

Thirteen of the women whose plasma MBP levels were followed from 32 weeks to term also displayed a similar late rise in MBP level. All of these women experienced a spontaneous onset of labor. In the four women who delivered at 38 weeks, MBP increases were evident at 35±0.6 weeks. In those four women whose labor began at 41 weeks, MBP concentration changes were not detectable before 38 weeks. One woman who entered premature labor at 34 weeks also exhibited a 35% spike in the plateau MBP level at that point.

Three women in the study failed to enter spontaneous labor and were oxytocin-induced at 42 weeks gestation. This dating was based on confident last menstrual period dates and ultrasound analysis. A late rise in MBP concentration was absent in all of these women.

Figure 2:
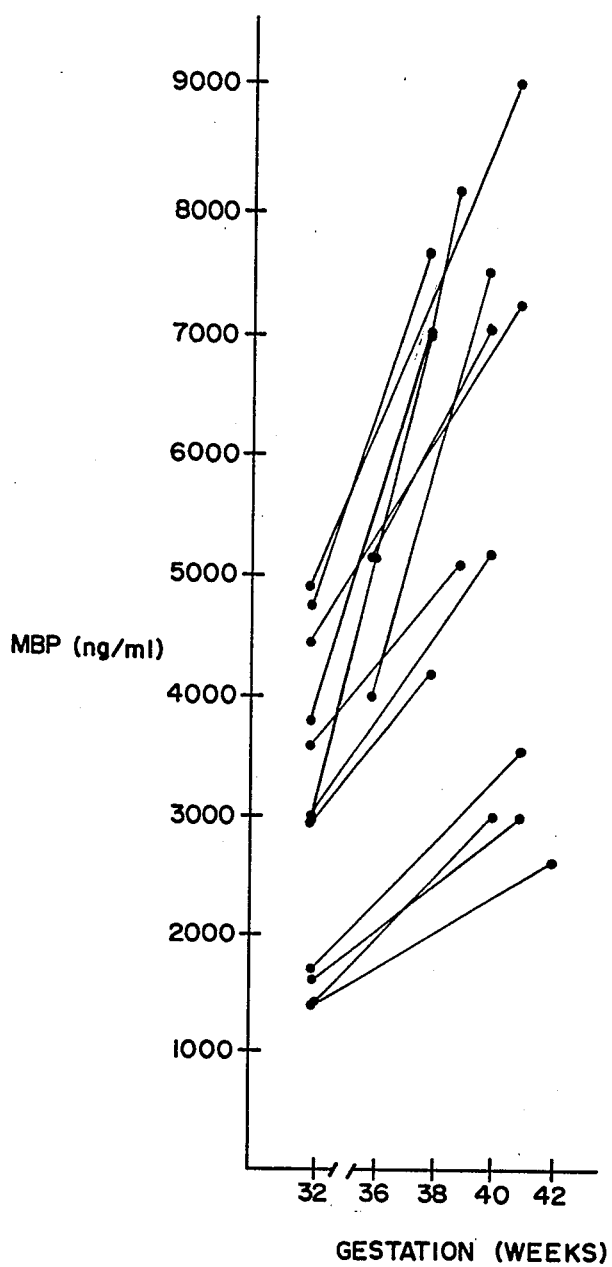
FIG. 2 is a graphical depiction of the late-term rise in MBP levels determined for 14 women who entered spontaneous labor.
Figure 3:
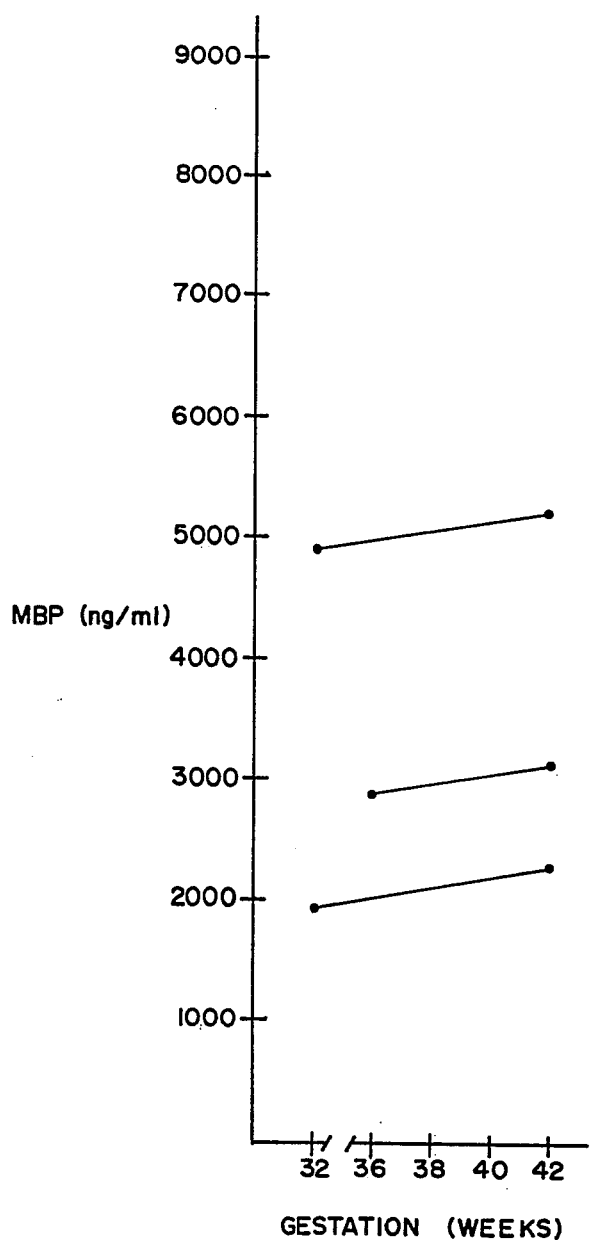
FIG. 3 is a graphic depiction of the late-term MBP levels for three women wherein labor was induced.

FIGS. 2 and 3 summarize the plasma MBP level data for the seventeen women studies. In the spontaneous labor group (FIG. 2), the late rise in the plateau MBP levels constituted 42±6.6% of the peak MBP levels seen at term which averaged 5720±2257 ng MBP/ml. In the oxytocininduced women (FIG. 3), MBP concentrations changed less than 10% (which is within the variability of the assay) and peak MBP levels at term averaged 3529±1533 ng/ml. Both groups displayed a wide variation in maximal MBP levels. Therefore, it is clear that a relative change in MBP level rather than a given absolute level is associated with the onset of labor.

The mean postpartum half-life for MBP in these 17 women (calculated using regression analysis) is 12.5±1.9 days (range=10.1-16.1 days).

The present invention has been exemplified with respect to the measurement of the relative MBP levels in plasma. However, due to our discovery of immunoreactive MBP in the urine of pregnant women which can be readily detected by RIA without reduction and alkylation, it is believed that other physiological fluids can be employed in the present method.

The invention has been described with reference to various specific and preferred embodiments and techniques. However, it should be understood that many variations and modifications may be made while remaining within the spirit and scope of the invention.

What is claimed is:

1. A method for determining the imminence of the onset of spontaneous labor in a pregnant woman comprising:
    (a) measuring the levels of esoinophil major basic protein (MBP) in a series of samples of a physiological fluid obtained from a pregnant woman after about 20 weeks of pregnancy and before labor begins;
    (b) averaging the levels determined in step (a) to determine the plateau gestational level of MBP in the physiological fluid of the pregnant woman; and
    (c) subsequently measuring the MBP level in a sample of said physiological fuid and determining whether a rise in the MBP level in said sample above the plateau gestational MBP level has occurred which is at least about 25-30% of the plateau gestational MBP level, wherein said rise is indicative of the imminent onset of spontaneous labor in said pregnant woman.

2. The method of claim 1 wherein the plateau average gestational MBP level is determined at about 20-33 weeks of pregnancy.

3. The method of claim 1 wherein the physiological fluid is blood plasma or blood serum.

4. The method of claim 1 wherein the physiological fluid is urine.

* * * * *

UNITED STATES PATENT AND TRADEMARK OFFICE
CERTIFICATE OF CORRECTION

PATENT NO. : 4,710,475

DATED : December 1, 1987

INVENTOR(S) : Gerald J. Gleich, Terri L. Wasmoen and Carolyn B. Coulam

It is certified that error appears in the above-identified patent and that said Letters Patent is hereby corrected as shown below:

On page 1, after "both of Rochester, Minn." add --Carolyn B. Coulam, Indianapolis, Ind.--.

Col. 1, line 7, for "the subjet of intense" read --the subject of intense--.

Col. 3, line 59, for "In one women, blood" read --In one woman, blood--.

Col. 4, line 29, for "unknown plasma and" read --unknown plasmas and--.

Col. 4, line 55, for "were analyed using" read --were analyzed using--.

Col. 5, line 30, for "the oxytocininduced women" read --the oxytocin-induced women--.

Col. 6, line 33, claim 2, for "the plateau average gestational" read --the plateau gestational--.

UNITED STATES PATENT AND TRADEMARK OFFICE
CERTIFICATE OF CORRECTION

PATENT NO. : 4,710,475

DATED : December 1, 1987

INVENTOR(S) : Gerald J. Gleich, Terri L. Wasmoen and Carolyn B. Coulam

It is certified that error appears in the above-identified patent and that said Letters Patent is hereby corrected as shown below:

Col. 6, line 27, claim 1(c), for "physiological fuid and" read --physiological fluid and--.

Signed and Sealed this

Tenth Day of May, 1988

Attest:

DONALD J. QUIGG

Attesting Officer

Commissioner of Patents and Trademarks